(12) United States Patent
Grimm et al.

(10) Patent No.: US 6,925,339 B2
(45) Date of Patent: Aug. 2, 2005

(54) IMPLANT REGISTRATION DEVICE FOR SURGICAL NAVIGATION SYSTEM

(75) Inventors: James E. Grimm, Winona Lake, IN (US); Shawn E. McGinley, Fort Wayne, IN (US)

(73) Assignee: Zimmer Technology, Inc., Chicago, IL (US)

( * ) Notice: Subject to any disclaimer, the term of this patent is extended or adjusted under 35 U.S.C. 154(b) by 18 days.

(21) Appl. No.: 10/357,754

(22) Filed: Feb. 4, 2003

(65) Prior Publication Data

US 2004/0153191 A1 Aug. 5, 2004

(51) Int. Cl.[7] .......................... G05B 19/18; A61B 19/00
(52) U.S. Cl. ........................ 700/59; 700/57; 606/130
(58) Field of Search ........................ 700/56–59, 114, 700/254; 606/130

(56) References Cited

U.S. PATENT DOCUMENTS

| | | | |
|---|---|---|---|
| 5,230,338 A | 7/1993 | Allen et al. | 128/653 |
| 5,251,127 A | 10/1993 | Raab | 364/413.13 |
| 5,305,203 A | 4/1994 | Raab | 364/413.13 |
| 5,326,376 A | 7/1994 | Warner et al. | 623/23 |

(Continued)

FOREIGN PATENT DOCUMENTS

| | | |
|---|---|---|
| EP | 1226788 | 7/2002 |
| WO | WO 98/32387 | 7/1998 |
| WO | WO 02/00145 | 1/2002 |

OTHER PUBLICATIONS

Provisional: U.S. Appl. No. 60/437,534.*

*Primary Examiner*—Leo Picard
*Assistant Examiner*—Elliot Frank
(74) *Attorney, Agent, or Firm*—Jonathan D. Feuchtwang; Baker & Daniels

(57) ABSTRACT

A system for registering an orthopedic implant in a computer assisted navigation system. The system includes a plurality of differently sized implants which may be the femoral component or hip stem of a prosthetic hip joint. A registration device is engageable with each of the implants in a predefined relative position. The registration device also includes at least one reference element registerable in the computer assisted navigation system. A second reference structure also having at least one reference element registerable in the computer assisted navigation system is detachably secured to the implant. The relative positions of the reference elements located on the registration device and second reference structure differs for each of the plurality of implants and thereby allows the navigation system to determine the nominal size of the implant. The relative position and orientation of the implant relative to the second structure can also be calibrated using the registration device.

20 Claims, 3 Drawing Sheets

U.S. PATENT DOCUMENTS

| | | | |
|---|---|---|---|
| 5,480,453 A | 1/1996 | Burke | 623/23 |
| 5,551,429 A | 9/1996 | Fitzpatrick et al. | 128/653.1 |
| 5,682,886 A | 11/1997 | Delp et al. | 128/653.1 |
| 5,871,018 A | 2/1999 | Delp et al. | 128/898 |
| 5,904,691 A | 5/1999 | Barnett et al. | 606/130 |
| 5,913,820 A | 6/1999 | Bladen et al. | 600/407 |
| 5,921,992 A | 7/1999 | Costales et al. | 606/130 |
| 5,995,738 A | 11/1999 | DiGioia, III et al. | 395/500.32 |
| 6,002,859 A | 12/1999 | DiGioia, III | |
| 6,033,415 A | 3/2000 | Mittelstadt et al. | 606/130 |
| 6,096,050 A | 8/2000 | Audette | 606/130 |
| 6,167,145 A | 12/2000 | Foley et al. | 382/128 |
| 6,236,875 B1 | 5/2001 | Bucholz et al. | 600/407 |
| 6,249,713 B1 * | 6/2001 | Geiger et al. | 700/57 |
| 6,285,902 B1 | 9/2001 | Kienzle, III et al. | 600/427 |
| 6,348,058 B1 | 2/2002 | Melkent et al. | 606/130 |
| 6,381,485 B1 | 4/2002 | Hunter et al. | |
| 6,396,939 B1 | 5/2002 | Hu et al. | 382/128 |
| 6,402,762 B2 | 6/2002 | Hunter et al. | 606/130 |
| 6,430,434 B1 | 8/2002 | Mittelstadt | 600/426 |
| 6,434,507 B1 | 8/2002 | Clayton et al. | 702/152 |
| 6,450,978 B1 | 9/2002 | Brosseau et al. | 600/595 |
| 6,470,207 B1 | 10/2002 | Simon et al. | 600/426 |
| 6,474,341 B1 | 11/2002 | Hunter et al. | 128/899 |
| 6,477,400 B1 | 11/2002 | Barrick | 600/426 |
| 6,490,467 B1 | 12/2002 | Bucholz et al. | 600/407 |
| 6,491,699 B1 | 12/2002 | Henderson et al. | 606/130 |
| 6,493,573 B1 | 12/2002 | Martinelli et al. | 600/424 |
| 6,499,488 B1 | 12/2002 | Hunter et al. | 128/899 |
| 6,697,664 B2 * | 2/2004 | Kienzle, III et al. | 600/427 |
| 6,711,431 B2 * | 3/2004 | Sarin et al. | 600/426 |
| 2002/0077543 A1 * | 6/2002 | Grzeszczuk et al. | 600/424 |
| 2004/0039402 A1 * | 2/2004 | Zeiss et al. | 606/130 |
| 2004/0054489 A1 * | 3/2004 | De La Barrera et al. | 702/105 |
| 2004/0097952 A1 * | 5/2004 | Sarin et al. | 606/102 |

* cited by examiner

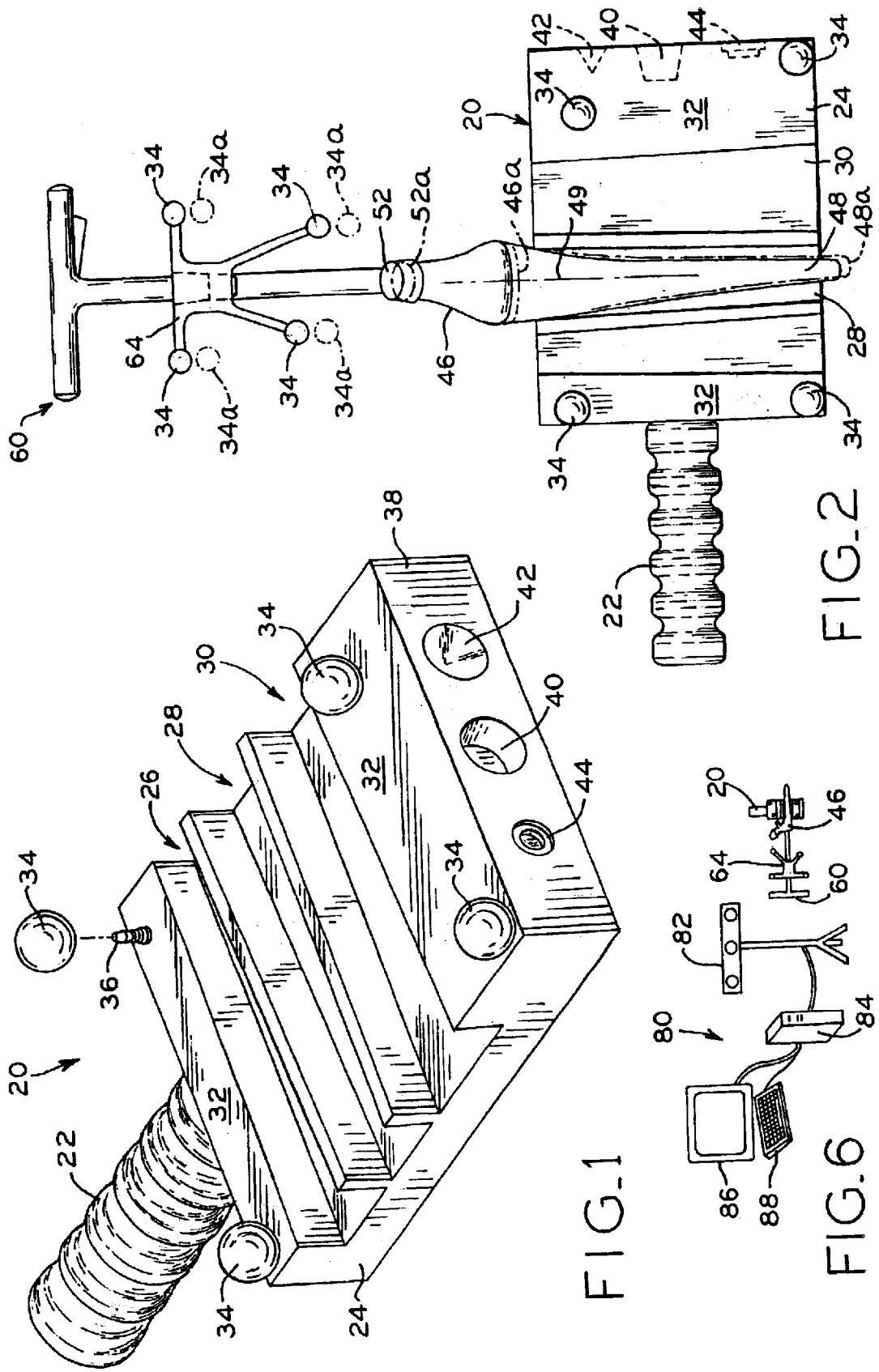

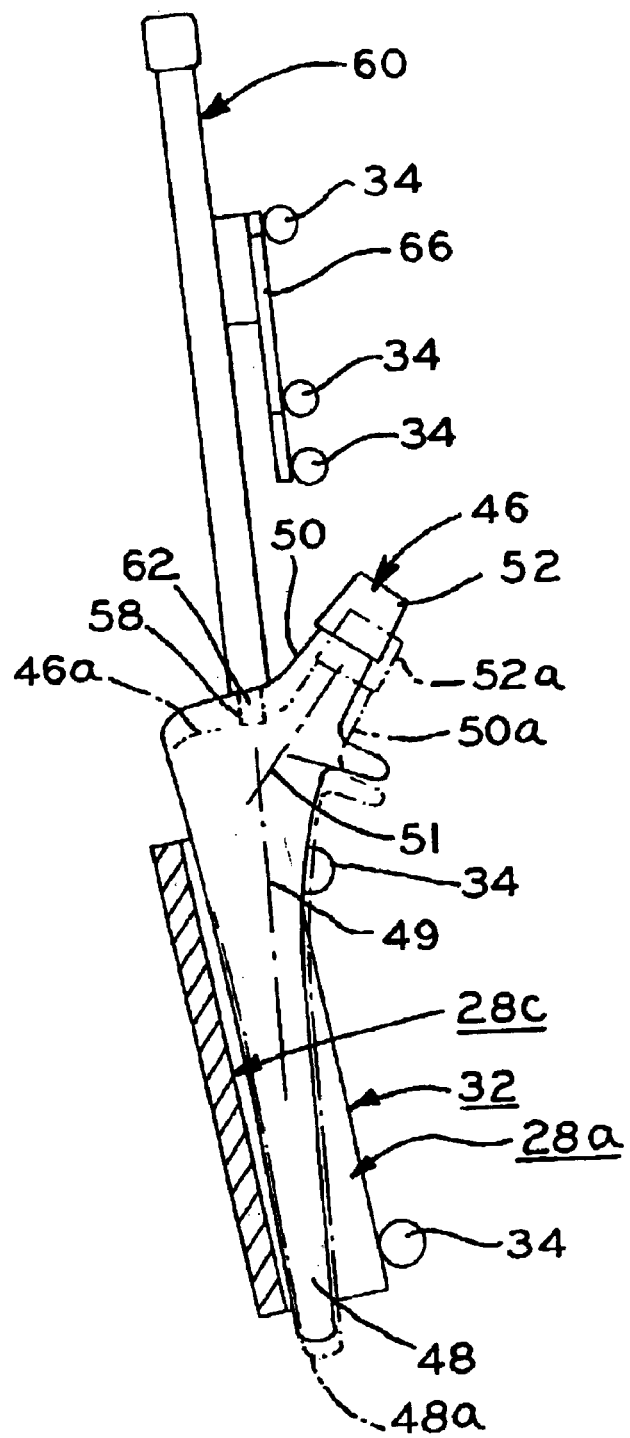
FIG_2A

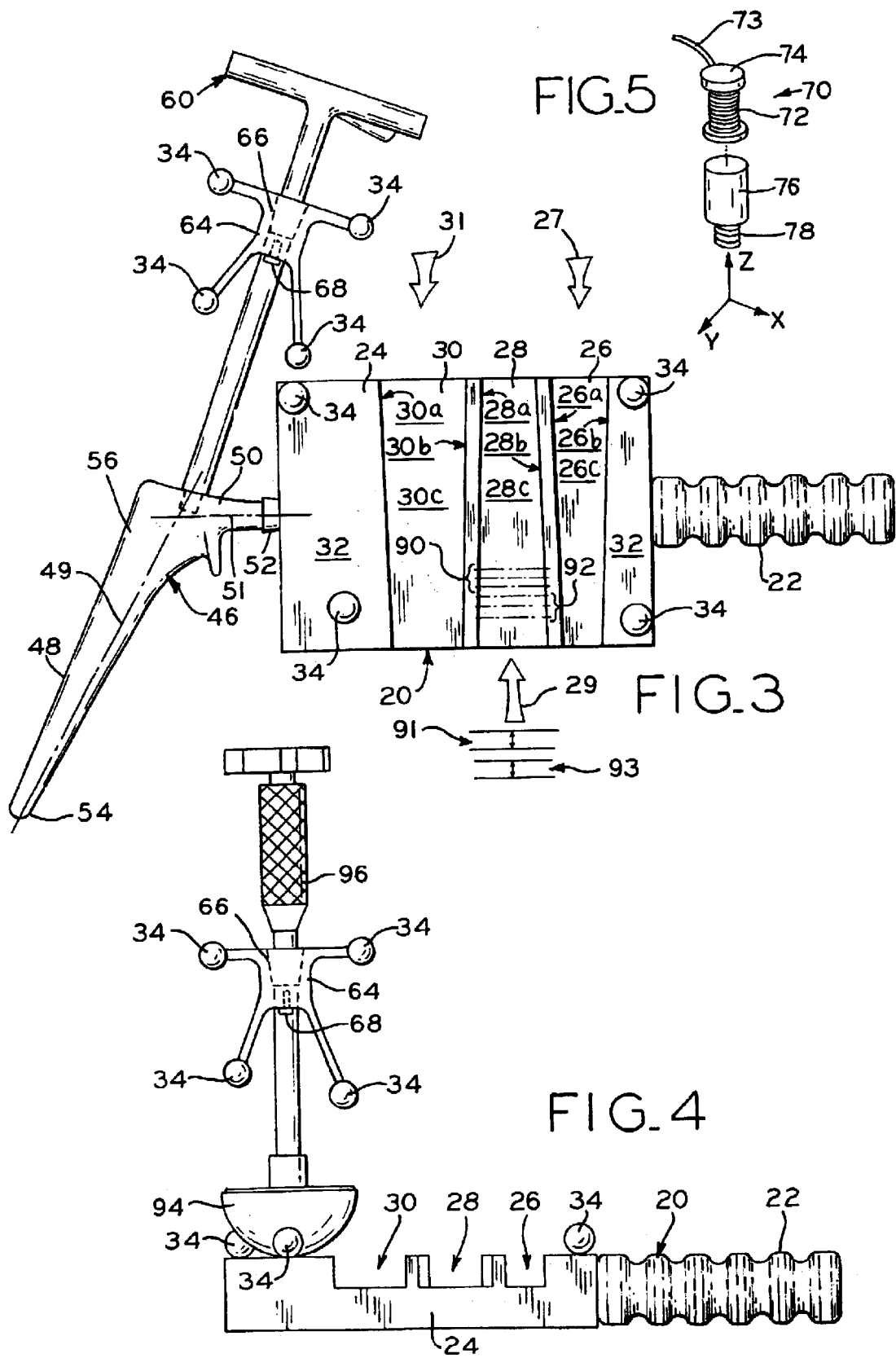

IMPLANT REGISTRATION DEVICE FOR SURGICAL NAVIGATION SYSTEM

BACKGROUND OF THE INVENTION

1. Field of the Invention

The present invention relates to a registration device and, more specifically, to a device for registering the position of an orthopedic implant in a computer assisted surgical navigation system.

2. Description of the Related Art

The controlled positioning of surgical instruments and other objects is of significant importance in many surgical procedures and various methods have been developed for properly positioning an object during a surgical procedure. Such methods include the use of both mechanical guides and computer assisted navigational systems. Computer assisted navigational techniques typically involve acquiring preoperative images of the relevant anatomical structures and generating a data base which represents a three dimensional model of the anatomical structures. The relevant tools and other objects used in the surgical procedure typically have a known and fixed geometry which is also defined preoperatively. During the surgical procedure, the position of the object being used is registered with the anatomical coordinate system and a graphical display showing the relative positions of the object and anatomical structure may be computed in real time and displayed for the surgeon to assist the surgeon in properly positioning and manipulating the object with respect to the relevant anatomical structure.

In such image guided procedures, a robotic arm may be used to position and control the object, or, the surgeon may manually position the object and use the display of the relative position of the object and anatomical structure to position the object. Examples of various computer assisted navigation systems which are known in the art are described in U.S. Pat. Nos. 5,682,886; 5,921,992; 6,096,050; 6,348,058 B1; 6,434,507 B1; 6,450,978 B1; 6,490,467 B1; and 6,491,699 B1 the disclosures of each of these patents is hereby incorporated herein by reference.

SUMMARY OF THE INVENTION

The present invention provides a registration device which is engageable with a plurality of differently sized orthopedic implants. The registration device is engageable with each of the implants in a predefined relative position. A first reference structure is disposed on the registration device and a second reference structure is detachably secured to the implant. Each of the first and second reference structures have at least one reference element registerable in a computer assisted navigation system whereby the position and/or orientation of the implant relative to the second reference structure may be determined or calibrated. After calibrating the position of the implant relative to the second reference structure, the registration device is disengaged from the implant. The second reference structure may be mounted on a handling tool which is then used to place the implant in its implanted position using the computer assisted navigational system.

The invention comprises, in one form thereof, a system for registering an orthopedic implant in a computer assisted navigation system. The system includes a plurality of differently sized implants and a registration device engageable with each of the plurality of implants in a first predefined relative position. The system also includes a first reference structure and a second reference structure. Each of the reference structures has at least one reference element registerable in the computer assisted navigation system. The first reference structure is disposed on the registration device at a predetermined location and the second reference structure is detachably securable to each of the plurality of implants. The relative positions of the first and second reference structures differs for each of the plurality of implants when the registration device is engaged at the first predefined location and the second reference structure is secured to a selected one of the implants.

The first and second reference structures may include at least three non-linearly positioned reference elements. The reference elements of the first and second reference structures may define first and second patterns which are distinguishable. The second reference structure may also be mounted on a handling tool that has an attachment feature detachably securable to each of the plurality of implants.

The implants may be a plurality of hip stems adapted for insertion in a proximal femur. The hip stems may have a generally L-shaped configuration defining a stem portion and a neck portion. The stem portion has a distal end and a proximal end. Each of the hip stems also includes a mounting interface located proximate the proximal end which is securable to the handling tool. The registration device includes at least one graduated space for receiving a distal end of a first one and a second one of the plurality of hip stems. The first and second hip stems engage the registration device within the at least one graduated space whereby the engagement features of said first and second hip stems are respectively positioned at first and second non-equivalent distances from the first reference structure. Each of the hip stems may also include a projection disposed on the neck portion wherein each of the projections has a common configuration. The reference member may include an engagement feature for engaging the projections at a predefined second relative position.

The invention comprises, in another form thereof, a system for registering an orthopedic implant in a computer assisted navigation system wherein the implant is adapted for implantation on a bone. The system includes a plurality of differently sized orthopedic implants, each of the implants having an elongate stem defining a stem axis and a registration device engageable with the stem of each of the plurality of implants at a first predefined relative position along the stem axis of each of the plurality of implants. A first reference structure having at least one reference element registerable in the computer assisted navigation system is disposed on the registration device at a predetermined location. The registration device may include at least one graduated engagement feature for engaging the stems at the first predefined relative position.

The invention comprises, in yet another form thereof, a method of registering an orthopedic implant in a computer assisted navigation system. The method includes providing a implant having a stem defining a stem axis. The stem has a distal end and a proximal end wherein the distal end has a smaller cross sectional area than the proximal end. A registration device including a first reference structure having at least one reference element registerable in the computer assisted navigation system is also provided. The registration device is engageable with the stem at a predefined axial location. The method includes attaching handling tool to the implant. The handling tool has a second reference structure mounted thereon. The second reference structure includes at least one reference element registerable in the computer assisted navigation system. The method also includes engaging the registration device with the implant at the predefined axial location with the implant secured to the handling tool and registering the positions of the first and second structures in the computer assisted navigation system and determining the position of implant stem relative to second reference structure.

The method may also include the step of disengaging the registration device from the implant stem following the step of determining the position of the implant stem relative to the second reference structure. The implant may also include a projection extending at an angle to the stem axis and the method further include the steps of engaging the reference device with the projection at a predefined relative position, registering the relative positions of the first and second reference structures in the computer assisted navigation system, and determining the rotational position of the projection relative to the stem axis.

In alternative embodiments of the method, a plurality of implants may be provided with each of the implants having a differently sized stem defining a stem axis. The stems may be tapered. Each stem has a distal end and a proximal end wherein the distal end has a smaller cross sectional area than the proximal end. The handling tool is attachable to each of the implants at a predefined location and the method also includes the steps of selecting one of the implants for attachment to the handling tool and engagement with the registration device. The step of determining the position of the implant stem relative to the second structure also includes determining the size of the selected implant based upon the distance between the first and second reference structures. The registration device may define at least one graduated space and the step of engaging the registration device with the implant includes inserting the tapered stem into the graduated space.

The invention comprises, in yet another form thereof, an assembly for use in a computer assisted navigation system. The assembly includes an orthopedic implant, at least one wire loop removably mounted on said orthopedic implant and a communication means operably coupled between the wire loop and the computer assisted navigation system and communicating a signal from the wire loop to the navigation system indicative of the magnetic field sensed by the wire loop.

The communication means may be a communications cable operably coupled to the wire loop. The at least one wire loop may be at least two wire loops, each of the loops defining a loop axis, the loops disposed in relatively fixed locations wherein the loop axes are positioned in a mutually perpendicular orientation. The wire loop may be mounted on a surgical instrument attached to the implant.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 1 is a perspective view of a registration device in accordance with the present invention.

FIG. 2 is a top view of the registration device with a hip stem inserted into a registration slot.

FIG. 2A is cross sectional view of FIG. 2 taken through the slot having a hip stem inserted therein.

FIG. 3 is a top view of the registration device with the neck of a hip stem inserted into a registration opening.

FIG. 4 is a side view of the registration device engaged with an acetabular cup.

FIG. 5 is an exploded schematic representation of an alternative embodiment of a reference element.

FIG. 6 is a schematic representation of a computer assisted navigation system and the registration device engaged with a hip stem.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DESCRIPTION OF THE PRESENT INVENTION

A registration device 20 in accordance with the present invention, is shown in FIG. 1. Registration device 20 includes a grip or handle portion 22 and a body 24. Three differently sized tapered slots 26, 28, 30 are formed in body 24. Each of the slots are defined by two opposed side surfaces 26a, 26b; 28a, 28b; 30a, 30b and a bottom surface 26c, 28c, 30c and define a compound taper. Mounted on the substantially planar upper surface 32 of body 24 are four referencing elements 34. In the illustrated embodiment, referencing elements 34 are reflective spheres which are registerable in a computer assisted navigation system as discussed in greater detail below. As can be seen in FIG. 1, body 24 forms an integral reference structure having reference elements 34 mounted thereon in fixed locations. Reference elements 34 are mounted on posts 36 projecting from body 24.

On the distal edge 38 of body 24 opposite handle 22 are three depressions 40, 42 and 44. Depression 40 is configured to closely fit the neck stem of a hip implant. Depression 42 has a conical shape and depression 44 has two concentric cylindrical portions of differing diameters. The illustrated registration device is formed of a stainless steel material, however, other suitable materials such as aluminum or plastic materials may also be used.

As best seen in FIG. 2, registration device 20 may be engaged with a femoral component of a prosthetic hip joint, i.e., hip stem 46. Examples of hip stems that may be used with the present invention are disclosed in U.S. Pat. Nos. 5,480,453 and 5,326,376 which are both hereby incorporated herein by reference. Hip stem 46 has a generally L-shaped configuration and includes an elongate stem portion 48 defining a stem axis 49 and a neck portion 50 defining a neck axis 51. A projection 52 is located on the neck and a prosthetic ball is mounted thereon for positioning in an acetabular cup. Typically, hip stems are manufactured in various sizes wherein the overall configuration of the hip stem remains substantially constant and proportional but the dimensions are varied to provide a range of sizes to fit differently sized patients.

FIGS. 2 and 2A illustrate a first implant 46 and a second implant 46a in dashed lines. First and second hip stems 46, 46a have a common design but are different sizes with second hip stem 46a being slightly smaller than hip stem 46. In the illustrated embodiment, projections 52, 52a are identical in size and shape to provide a common mounting interface between the hip stems and femoral balls. Additionally, the stems are tapered and distal end 54 has a smaller cross sectional area than proximal end 56 of stem 48. The illustrated stems have a compound taper defining two taper angles.

Each of the hip stems 46 also includes a mounting interface which is located on the proximal edge of the hip stem near proximal end 56 of stem 48. Hip stems typically include such mounting interfaces which are used to removably attach the hip stem to a handling tool, often referred to as a stem inserter. A variety of such interfaces are known. For example, mounting interface 58 on stem 46 may be a threaded bore with handling tool or stem inserter 60 having a threaded shaft 62 which threadingly engages bore 58 to secure hip stem 46 to handling tool 60 in a manner known in the art. After attaching stem inserter 60 to hip stem 46, stem inserter 60 is used to manipulate hip stem 46 instead of directly handling hip stem 46. Stem inserter 60 is removed from hip stem 46 after positioning hip stem 46 in its final implanted position in a femur.

A rigid aluminum reference structure 64 having reference elements 34 mounted thereon in fixed relative positions is secured to stem inserter 60. A dovetail joint 66 is used to removably mount reference structure 64 on stem inserter 60. A threaded fastener 68 firmly secures reference structure 64 in a desired location on stem inserter 60. In alternative embodiments, reference structure 64 may be permanently affixed to stem inserter 60 or be formed integrally therewith.

The underlying handling tool structure on which reference structure 64 is mounted at a predefined location may be a conventional handling tool. Although the illustrated embodiment utilizes a threaded shaft to secure tool 60 to implant 46 other attachment features for securing the handling tool to the implant may be used. For example, the implant may have a smooth walled bore and the handling tool may have an expandable collet which may be releasably secured within the bore. Moreover, the present invention may be used with alternative implants, e.g., for a prosthetic knee joint, and handling tools adapted for use with such implants.

Examples of handling tools that may have reference structures mounted thereon and used with the present invention are described by Hoag et al. in U.S. patent application Ser. No. 10/194,874 entitled TOOL FOR GRIPPING AN ORTHOPEDIC IMPLANT filed on Jul. 12, 2002 and by Hoag et al. in U.S. patent application Ser. No. 10/194,744 entitled TOOL FOR RELEASABLY GRIPPING AN ORTHOPEDIC IMPLANT filed on Jul. 12, 2002 the disclosures of both of these applications is hereby incorporated herein by reference.

In addition to its stem handling function, by mounting reference structure 64 thereon, stem inserter 60 also serves to detachably secure reference structure 64 to stem 46 in a relative position which will be generally fixed until stem inserter 60 is disengaged from stem 46. As discussed below, registration block 20 may be used to determine the relative position of hip stem 46 to reference structure 64 after attaching stem inserter 60 to hip stem 46 thereby allowing a computer assisted navigation system to track hip stem 46 by sensing the location and orientation of reference structure 64.

In other embodiments of the present invention, a reference structure having one or more reference elements may be directly and removably mounted to the implant instead of via a handling tool. Such a directly attached reference structure would provide for the tracking of the implant but not provide the handling function provided by tool 60.

The position of hip stem 46 must be calibrated with the position of reference structure 64 for computer assisted navigation system 80 to accurately track the position and orientation of hip stem 46. The use of registration device 20 to perform such a calibration will now be described.

Registration device 20 has three tapered slots 26, 28, 30 wherein the opposed side surfaces of the slots, e.g., surfaces 28a, 28b, define a graduated space therebetween. The space defined by slots 26, 28, 30 are configured to uniquely engage registration device 20 with each of the differently sized hip stems 46 for which registration device 20 is intended for use.

In the illustrated embodiment, registration device 20 has been configured for use with a line of hip stems having approximately ten different nominal sizes. Each of the slots 26, 28, 30 are configured for use with 3 or 4 different nominal sizes, i.e., slot 26 receives the smallest sizes, slot 28 the middle sizes and slot 30 the largest sizes. As best seen in FIG. 3, stems 48 are inserted into slots 26, 28, 30 in the directions indicated by arrows 27, 29, 31 respectively.

The dimensional tolerances inherent in the manufacture of stems 46 will result in a particular nominal size of a stem 46 being engaged with its associated slot within a narrow band. For example, the group of lines indicated by reference numeral 90 shown in FIG. 3 represent the two extremes and midpoint of where implant 46a would engage slot 28 based upon the manufacturing tolerances of stem 46a. These engagement locations translate into a range 91 which indicates the location of the engagement interface between stem 46a and handling tool 60. Similarly, lines 92 indicate the two extremes and midpoint of where implant 46 would engage surfaces 28a and 28b and range 93 indicates the location of the engagement interface between stem 46 and handling tool 60. This can also be seen with reference to FIGS. 2 and 2A which illustrate implant 46 engaged in the predefined relative position represented by lines 92 (lines 92 are only shown in FIG. 3) and an outline of smaller implant 46a engaged in the predefined relative position represented by lines 90 (lines 90 are only shown in FIG. 3).

Slots 26, 28, 30 are configured so that the ranges 91, 93 of the engagement interface between implant and handling tool of the differently sized implants do not overlap. Because the same tool 60 is used to engage each implant 46, each different nominal size of implant 46 defines a range of positions of reference structure 64, relative to registration device 20, which is unique and does not overlap the range of any other nominal size of implant 46. This is exemplified in FIG. 2 which illustrates the reference elements 34 disposed on handling tool 60 in solid lines to represent their relative position when implant 46 is engaged with registration device 20 and in dashed outlines 34a to represent their relative position when smaller nominal sized implant 46a is engaged with registration device 20. By configuring registration device 20 so that there is no overlap in the range of positions of reference structure 64 for the different nominal sizes of implants 46, navigation system 80 can determine the nominal size of the implant after inserting its stem into the appropriate slot 26, 28, 30 on registration device 20. The dimensions of the various nominal sizes of implants 46 are entered into the navigation system 80 prior to engaging registration device 20 with an implant 46.

Although the illustrated embodiment utilizes tapered slots, alternative graduated engagement features could also be employed with the present invention. For example, in alternative embodiments, the orthopedic implant might include surface defining a space therebetween and the registration device might include a graduated projection which fit within the space to engage the implant at a predefined position relative to the implant.

As best seen in FIGS. 2 and 2A, the axis of stem inserter 60 is positioned coaxially with stem axis 49 of an attached hip stem 46. Thus, when stem 48 is engageably inserted into one of slots 26, 28, 30 and the relative positions of the reference structures 24, 64 respectively located on calibration paddle 20 and stem inserter 60, the processor of computer assisted navigation system 80 may calculate the nominal size of hip stem 46, the orientation of stem axis 49, the position of hip stem along the line defined by axis 49, i.e., the axial position of hip stem 46. It does not, however, calculate the rotational or angular orientation of neck 50 relative to axis 49 when stem 48 is inserted in one of the slots 26, 28, 30. As shown in FIG. 2A, the illustrated embodiment of registration device 20 is configured so that neck 50 of hip stems 46 project in the same direction that reference elements 34 project from surface 32.

To determine he angular orientation of neck 50, stem 48 is removed from slot 28 and projection 52 is engaged with device 20 by insertion into depression 40. Depression 40 has slightly tapered sidewalls which match the taper on the common configuration of projections 52 located on implants 46. By flushly engaging projection 52 of the stem 46 secured to handling tool 60 with depression 40 as shown in FIG. 3, the rotational position of projection 52 and neck 50 about axis 49 and relative to reference structure 64 can be determined by navigational system 80 from the relative positions of body 24 and reference structure 64.

When used with an optical tracking system, registration device 20 and reference structure 64 require at least three non-linearly positioned reference points to define the location and orientation of the reference structure on which the reference points are located. The pattern defined by the reference elements disposed on registration device 20 and reference structure 64 may also differ whereby navigation system 80 may more readily distinguish and identify the object associated with each set of reference elements.

The registration device may be used to calibrate the position of other objects in a computer assisted navigation system in addition to hip stems 46. For example, FIG. 4 illustrates an acetabular cup 94 placed in engagement with the substantially planar surface 32 which has a known orientation to the reference structure defined by reference elements 34 mounted on body 24. A handling tool 96 adapted for engaging cup 94 has a reference structure 64 mounted thereon and registration device 20 may be used in the calibration of the reference structure 64 mounted on handling tool 96 which is otherwise a conventional instrument for handling an acetabular cup during the implantation thereof as is known in the art. When tool 96 is secured to acetabular cup 94, the distance of reference structure 64 from surface 32 will be dependent upon the nominal size of the acetabular cup 94. Thus, the registration of cup 94 with surface 32 may be used to verify that the correct size of cup 94 has been mounted on instrument 96 prior to implanting cup 94.

Similarly, depressions 42 and 44 have a known location and orientation relative to elements 34 mounted on body 24 and may be used to calibrate the coordinates of various surgical instruments or objects within a computer assisted navigation system. For example the tip of a digitizing probe, reamer, awl or other object could be engaged with a selected one of the depressions 42, 44.

Returning to the implantation of a hip stem 46, the proper positioning of the hip stem in the femur is of great importance with respect to re-establishing the proper leg length of the patient. As is known in the art, the relevant dimensional data concerning an anatomical structure of interest, e.g., a femur, may be determined using data acquired from images of the anatomical structure to generate a data base representing a model of the anatomical structure. The model of the anatomical structure may be a three dimensional model which is developed by acquiring a series of two dimensional images of the anatomical structure. Alternatively, the model of the anatomical structure may be a set of two dimensional images having known spatial relationships or other data structure which can be used to convey information concerning the three dimensional form of the anatomical structure. The model of the anatomical structure may then be used to generate displays of the anatomical structure from various perspectives for preoperative planning purposes and intraoperative navigational purposes. A variety of technologies which may be employed to generate such a model of an anatomical structure are well known in the art and include computed tomography (CT), magnetic resonance imaging (MRI), positron emission tomography (PET), ultrasound scanning and fluoroscopic imaging technologies.

The model of the anatomical structure obtained by such imaging technologies can be used for the intraoperative guidance of an implant by facilitating the determination and display of the relative position and orientation of the implant with respect to the actual anatomical structure. For example, if the model of the anatomical structure is a set of two dimensional images having known spatial relationships, several such images may be simultaneously displayed during the surgical procedure. By also displaying the position of the implant in the images and displaying images taken from different perspectives, e.g., one image facilitating the display of implant movement along the x and y coordinate axes and another image facilitating the display of implant movement along the z axis, the individual images may together represent the movement of the implant in three dimensions relative to the anatomical structure.

For reference purposes, a coordinate system defined by the actual anatomical structure which is the subject of interest will be referred to herein as the anatomical coordinate system and a coordinate system defined by the model of the anatomical structure will be referred to as the image coordinate system. Data concerning the fixed size and shape of the implant which will be used in the image guided procedure is also determined pre-operatively to obtain a three dimensional model of each of the different nominal sizes of the implant or the relevant portions thereof.

Rigid anatomical structures, such as skeletal elements, are well suited for such image guided surgical techniques and individual skeletal elements may be used to define separate coordinate systems. The different rigid structures, e.g., skeletal elements, may be subject to relative movement, for example, the femur and acetabulum of a patient may be relatively moved during the surgical procedure and separate three dimensional models and coordinate systems may be created for the different skeletal elements. For example, during a hip replacement procedure, a three dimensional model of the femur defining a first coordinate system may be utilized during the resection of the femur while a separate coordinate system defined by a three dimension model of the pelvis is utilized during the preparation of the acetabulum.

When using computer assisted navigation, also referred to as computer implemented image guidance, to conduct a surgical technique, the image coordinate system is registered with the anatomical coordinate system and the position of the implant or other tracked object is also registered within the image coordinate system. After the registration of both the actual anatomical structure and the implant, the relative position and orientation of the implant may be communicated to the surgeon by displaying together images of the anatomical structure and the implant based upon the three dimensional models of the anatomical structure and implant which were previously acquired.

Computer implemented image guidance systems which provide for the registration of an actual anatomical structure with a three dimensional model representing that structure together with the registration or localization of another object such as a surgical instrument or orthopedic implant within the image coordinate system to facilitate the display of the relative positions of the object and the actual anatomical structure are known in the art. Known methods of registering the anatomical structure with the image coordinate system include the use of implanted fiducial markers which are recognizable by one or more scanning technologies. Alternatively, implants which may be located by physically positioning a digitizing probe or similar device in contact or at a known orientation with respect to the implant. Instead of using fiducial implants, it may also be possible to register the two coordinate systems by aligning anatomical landmark features. U.S. Pat. Nos. 6,236,875 B1 and 6,167,145 both describe methods of registering multiple rigid bodies and displaying the relative positions thereof and the disclosures of both of these patents are hereby incorporated herein by reference.

Tracking devices employing various technologies enabling the registration or localization of a surgical instrument or other object such as an orthopedic implant and the tracking of the object motion with respect to the anatomical coordinate system, which has also been registered with the image coordinate system, are also known. For example, optical tracking systems which detect light from reflected or emitted by reflective targets or localizing emitters secured in a known orientation to the object are known for determining the position of an object and registering the position of the object within an image coordinate system representing a three dimensional model of an anatomical structure. For example, such a tracking system may take the form of a sensor unit having one or more lenses each focusing on separate charge coupled device (CCD) sensitive to infrared light. The sensor unit detects infrared light emitted by three or more non-linearly positioned light emitting diodes (LEDs) secured relative to the object. A processor analyzes the images captured by the sensor unit and calculates the position and orientation of the object. By registering the position of the sensing unit within the image coordinate system, the position of the object relative to the anatomical structure, which has also been registered with the image coordinate system, may be determined and tracked as the object is moved relative to the anatomical structure.

Alternative localizing systems may employ localizing emitters which emit an electromagnetic signal in the radio frequency or which emit visible light. Other types of localizing systems that could be used with the present invention employ referencing elements or other distinguishing elements which are radio-opaque. It is also possible to employ digitizing physical probes which are brought into physical contact with the object at predefined locations on the object to register the position of the object.

In the disclose embodiment, the localizing system includes a light source and reference elements 34 reflect the light. The localizing system then detects the reflected light and computes the location of the individual reference elements 34 in a known manner. Reference elements 34 may be obtained from Northern Digital Inc. having a place of business at 103 Randall Dr., Waterloo, Ontario, Canada, N2V1C5. Northern Digital Inc. supplies image guidance systems under the bra d names Optotrak® and Polaris® which may be used with the present invention. The present invention may also be used with other computer assisted navigation systems such as those described above or otherwise known in the art. For example, Medtronic, Inc. headquartered in Minneapolis, Minn. manufactures and sells various computer assisted surgical navigation systems under the trademark StealthStation® such as the FluoroNav™ Virtual Fluoroscopy System which could also be adapted for use with the present invention.

FIG. 6 schematically illustrates navigation system 80 which includes a position sensor 82 for detecting the position of reference elements 34 disposed on stem inserter 60 and registration device 20, processing unit 84, display screen 86 and input device 88.

An alternative embodiment of the present invention could be employed with a computer assisted navigation system which utilizes magnetic fields instead of optical tracking to determine the position and orientation of the tracked object. A variety of referencing elements which are used with magnetic fields which could be adapted for use with the present invention are known in the art. For example, known systems using magnetic fields to determine the position and orientation of an object are described by U.S. Pat. Nos. 5,913,820; 6,381,485 B1; 6,402,762 B2; 6,474,341 B1; 6,493,573 B1; and 6,499,488 B1 the disclosures of these patents are all hereby incorporated herein by reference.

FIG. 5 schematically illustrates a reference element 70 which takes the form of a wire loop, in this case a copper wire coil 72 wound about a polymeric bobbin 74 and disposed in a polymeric housing 76 which may be used in a magnetic field navigation system. The axis of wire loop 72 is defined by the cylindrical shaft of bobbin 74 about which wire coil 72 is wound. Housing 76 includes a threaded shaft 78 projecting from one end which provides for the mounting of housing 76 and wire loop 72 located therein. Wire loop 72 is in communication with the processor of a computer assisted navigation system via cable 73. Wireless communication between wire loop 72 and the processor using radio signals could alternatively be employed. Two or more such loops 72 may be advantageously fixed in mutually perpendicular orientations, e.g., each such loop may have an axis which is positioned parallel to one of the three axes of a Cartesian coordinate system. (In FIG. 5, wire loop 72 is shown having an axis which extends parallel to the Z axis.)

By generating a magnetic field of known properties in the operative area and sensing the field with mutually perpendicular wire loops 72, the position and orientation of the reference element defined by the loops 72 and the rigid object, such as a surgical instrument or orthopedic implant, attached thereto may be calculated. The determination of the position and orientation of such mutually perpendicularly oriented field sensors 72 is known in the art. It is also known to use a single wire loop 72 to form a field sensor and determine its position and orientation by generating magnetic fields from a plurality of locations.

In the illustrated embodiment, wire loop 72 is a cylindrical coil, however, other loop shapes may also be employed. A wire loop 72 may attached to a handling tool such as stem inserter 60 in a variety of methods. For example, a wire loop may be placed in a specially machined pocket and retained in place by a mechanical, adhesive, e.g., glue or epoxy, or other suitable means. It could also be mounted to an instrument or implant via a fixture that contains the loop such as housing 76 or a plastic screw that has a wire loop insert molded therein. Such a fixture would facilitate the mounting of the wire loop to existing instruments. The navigated instrument could also be manufactured with the coil integral to it or have a mounting for winding the wire loop thereon.

Such instruments could be manufactured using various materials such as metal, non-ferrous metal, plastic and composite materials. The choice of materials of such instruments and fixtures could facilitate the provision of single use disposable instruments or fixtures.

Other surgical tools which may be employed in a surgical procedure implanting a prosthetic hip joint and utilizing a computer assisted navigational system are described by McGinley et al. in a U.S. patent application entitled SURGICAL NAVIGATION INSTRUMENT USEFUL IN MARKING ANATOMICAL STRUCTURES having attorney docket No. ZIM0167 filed on the same date as the present application, and by McGinley et al. in a U.S. patent application entitled GUIDANCE SYSTEM FOR ROTARY SURGICAL INSTRUMENT having attorney docket No. ZIM0165 filed on the same date as the present application, the disclosures of both of these applications are hereby incorporated herein by reference.

While this invention has been described as having an exemplary design, the present invention may be further modified within the spirit and scope of this disclosure. This application is therefore intended to cover any variations, uses, or adaptations of the invention using its general principles.

What is claimed is:

1. A system for registering an orthopedic implant in a computer assisted navigation system, said system comprising:
    a plurality of differently sized implants;
    a registration device engageable with each of said plurality of implants in a first predefined relative position;
    a first reference structure and a second reference structure, each of said reference structures having at least one reference element registerable in the computer assisted navigation system, said first reference structure disposed on said registration device at a predetermined location, said second reference structure detachably securable to each of said plurality of implants;
    wherein the relative positions of said first and second reference structures differs for each of said plurality of implants when said registration device is engaged at said first predefined location and said second reference structure is secured to a selected one of said implants;
    wherein said second reference structure is detachably mounted on a handling tool at a predefined location, said handling tool having an attachment feature detachably securable to each of said plurality of implants;
    wherein said plurality of implants comprises a plurality of hip stems adapted for insertion in a proximal femur;
    wherein each of said plurality of differently sized hip stems has a generally L-shaped configuration defining a stem portion and a neck portion, said stem portion having a distal end and a proximal end and wherein each of said hip stems includes a mounting interface securable to said handling tool, said mounting interface located proximate said proximal end of said hip stem and wherein said registration device defining at least one graduated space for receiving a distal end of a first one and a second one of said plurality of hip stems, said first and second hip stems engaging said registration device within said at least one graduated space whereby said engagement features of said first and second hip stems are positioned at first and second distances from said first reference structure respectively, said first and second distances being non-equivalent.

2. The system of claim 1 wherein each of said first and second reference structures includes at least three non-linearly positioned reference elements.

3. The system of claim 1 wherein said first reference structure includes at least three non-linearly positioned reference elements defining a first pattern and said second reference structure includes at least three non-linearly positioned reference elements defining a second pattern, said first and second patterns being distinguishable.

4. The system of claim 1 wherein said plurality of implants comprises a plurality of hip stems adapted for insertion in a proximal femur.

5. The system of claim 1 wherein each of said plurality of hip stems includes a projection disposed on said neck portion, said projections having a common configuration, said reference member including an engagement feature for engaging said projections at a predefined second relative position.

6. A system for registering an orthopedic implant in a computer assisted navigation system, the implant being adapted for implantation on a bone, said system comprising:
    a plurality of differently sized orthopedic implants, each of said implants having an elongate stem defining a stem axis;
    a registration device engageable with said stem of each of said plurality of implants at a first predefined relative position along said stem axis of each of said plurality of implants;
    a first reference structure having at least one reference element registerable in the computer assisted navigation system, said first reference structure disposed on said registration device at a predetermined location, further comprising a second reference structure having at least one reference element registerable in the computer assisted navigation system, said second reference structure being detachably securable to each of said plurality of implants wherein each of said implants further comprises a projection extending at an angle to said stem axis and wherein said registration device further comprises an engagement feature engageable with each of said projections at a predefined second relative position wherein a rotational orientation of said projection relative to said stem axis is determinable.

7. The system of claim 6 wherein said first reference structure includes at least three non-linearly positioned reference elements.

8. The system of claim 6 wherein said plurality of implants comprises a plurality of hip stems adapted for insertion in a proximal femur.

9. A system for registering an orthopedic implant in a computer assisted navigation system, the implant being adapted for implantation on a bone, said system comprising:
    a plurality of differently sized orthopedic implants, each of said implants having an elongate stem defining a stem axis;
    a registration device engageable with said stem of each of said plurality of implants at a first predefined relative position along said stem axis of each of said plurality of implants;
    a first reference structure having at least one reference element registerable in the computer assisted navigation system, said first reference structure disposed on said registration device at a predetermined location wherein said registration device comprises at least one graduated space for engaging said stems.

10. The system of claim 9 further comprising a second reference structure having at least one reference element registerable in the computer assisted navigation system, said second reference structure being detachably securable to each of said plurality of implants.

11. The system of claim 9 further comprising a second reference structure having at least one reference element registerable in the computer assisted navigation system, said second reference structure being detachably mounted on a handling tool at a predefined location, said handling tool having an attachment feature detachably securable to each of said plurality o implants.

12. The system of claim 9 wherein said first reference structure includes at least three non-linearly positioned reference elements.

13. A system for registering an orthopedic implant in a computer assisted navigation system, the implant being adapted for implantation on a bone, said system comprising:
 a plurality of differently sized orthopedic implants, each of said implants having an elongate stem defining a stem axis;
 a registration device engageable with said stem of each of said plurality of implants at a first predefined relative position along said stem axis of each of said plurality of implants;
 a first reference structure having at least one reference element registerable in the computer assisted navigation system, said first reference structure disposed on said registration device at a predetermined location wherein said registration device comprises a plurality of differently sized graduated spaces for engaging said stems of said plurality of implants.

14. The system of claim 13 wherein said first reference structure includes at least three non-linearly positioned reference elements.

15. The system of claim 13 further comprising a second reference structure having at least one reference element registerable in the computer assisted navigation system, said second reference structure being detachably securable to each of said plurality of implants.

16. The system of claim 13 further comprising a second reference structure having at least one reference element registerable in the computer assisted navigation system, said second reference structure being detachably mounted on a handling tool at a predefined location, said handling tool having an attachment feature detachably securable to each of said plurality of implants.

17. A method of registering an orthopedic implant in a computer assisted navigation system, said method comprising:
 providing an implant having a stem defining a stem axis, said stem having a distal end and a proximal end wherein said distal end has a smaller cross sectional area than said proximal end;
 providing a registration device having a first reference structure, said first reference structure including at least one reference element registerable in the computer assisted navigation system, said registration device being engageable with said stem at a predefined axial location;
 attaching a handling tool to said implant, said handling tool having a second reference structure mounted thereon, said second reference structure including at least one reference element registerable in the computer assisted navigation system;
 engaging the registration device with the implant at the predefined axial location with said implant secured to said handling tool and registering the positions of said first and second structures in the computer assisted navigation system; and determining the position of implant stem relative to second reference structure;
 wherein said registration device defines at least one graduated space and said step of engaging the registration device with said implant includes inserting said tapered stem into said graduated space.

18. The method of claim 17 further comprising the step of disengaging the registration device from the implant stem following the step of determining the position of the implant stem relative to the second reference structure.

19. The method of claim 18 wherein said implant includes a projection extending at an angle to said stem axis and said method further comprises the steps of engaging the reference device with said projection at a predefined relative position and registering the relative positions of said first and second reference structures in said computer assisted navigation system; and determining the rotational position of said projection relative to said stem axis.

20. The method of claim 17 wherein a plurality of implants are provided, each of said implants having a differently sized tapered stem defining a stem axis, each said stem having a distal end and a proximal end wherein said distal end has a smaller cross sectional area than said proximal end, said handling tool being attachable to each of said implants at a predefined location; and wherein said method further includes the steps of selecting one of said implants for attachment to said handling tool and engagement with said registration device and said step of determining the position of the implant stem relative to said second structure further includes determining the size of the selected implant based upon the distance between said first and second reference structures.

* * * * *